US011814360B2

(12) United States Patent
Kulikov et al.

(10) Patent No.: US 11,814,360 B2
(45) Date of Patent: Nov. 14, 2023

(54) ISOCYANATES, DERIVATIVES, AND PROCESSES FOR PRODUCING THE SAME

(71) Applicant: Novomer, Inc., Rochester, NY (US)

(72) Inventors: Oleg Kulikov, Rochester, NY (US); Sadesh H. Sookraj, Cambridge, MA (US); Utpal Mahendra Vakil, West Henrietta, NY (US); Matthew Goodrich, Rochester, NY (US)

(73) Assignee: Novomer, Inc., Rochester, NY (US)

(*) Notice: Subject to any disclaimer, the term of this patent is extended or adjusted under 35 U.S.C. 154(b) by 895 days.

(21) Appl. No.: 16/753,591

(22) PCT Filed: Oct. 4, 2018

(86) PCT No.: PCT/US2018/054375
§ 371 (c)(1),
(2) Date: Apr. 3, 2020

(87) PCT Pub. No.: WO2019/070981
PCT Pub. Date: Apr. 11, 2019

(65) Prior Publication Data
US 2020/0331876 A1 Oct. 22, 2020

Related U.S. Application Data

(60) Provisional application No. 62/661,951, filed on Apr. 24, 2018, provisional application No. 62/568,511, filed on Oct. 5, 2017.

(51) Int. Cl.
| | | |
|---|---|---|
| *C07D 305/12* | (2006.01) | |
| *C07D 305/08* | (2006.01) | |
| *C07D 305/14* | (2006.01) | |
| *C07D 307/20* | (2006.01) | |
| *C07D 407/12* | (2006.01) | |
| *C08G 18/09* | (2006.01) | |
| *C08L 75/04* | (2006.01) | |
| *C07C 263/12* | (2006.01) | |
| *C08G 18/44* | (2006.01) | |
| *C08G 18/48* | (2006.01) | |
| *C07C 263/00* | (2006.01) | |
| *C07C 265/00* | (2006.01) | |

(52) U.S. Cl.
CPC .......... *C07D 305/12* (2013.01); *C07C 263/00* (2013.01); *C07C 263/12* (2013.01); *C07C 265/00* (2013.01); *C07D 305/08* (2013.01); *C07D 305/14* (2013.01); *C07D 307/20* (2013.01); *C07D 407/12* (2013.01); *C08G 18/09* (2013.01); *C08G 18/44* (2013.01); *C08G 18/48* (2013.01); *C08L 75/04* (2013.01)

(58) Field of Classification Search
CPC ... C07C 263/00; C07C 263/12; C07D 305/08; C08G 18/09
See application file for complete search history.

(56) References Cited

U.S. PATENT DOCUMENTS

| | | | |
|---|---|---|---|
| 829,251 | A | 8/1906 | Booraem |
| 2,375,005 | A | 5/1945 | Kung |
| 5,646,230 | A * | 7/1997 | Pantone ................ C08G 18/48 |
| | | | 252/182.2 |
| 8,445,703 | B2 | 5/2013 | Allen et al. |
| 8,796,475 | B2 | 8/2014 | Allen et al. |
| 9,156,803 | B2 | 10/2015 | Allen et al. |
| 9,206,144 | B2 | 12/2015 | Allen et al. |
| 9,327,280 | B2 | 5/2016 | Lee et al. |
| 9,403,788 | B2 | 8/2016 | Lee et al. |
| 9,493,391 | B2 | 11/2016 | Allen et al. |
| 9,718,755 | B2 | 8/2017 | Sookraj et al. |
| 9,719,037 | B2 | 8/2017 | Sookraj |
| 10,221,278 | B2 | 3/2019 | Lee et al. |
| 10,252,969 | B2 | 4/2019 | Farmer et al. |
| 10,479,861 | B2 | 11/2019 | Lee et al. |

(Continued)

FOREIGN PATENT DOCUMENTS

| | | | |
|---|---|---|---|
| JP | S48-102867 A | 12/1973 | |
| JP | S49-026231 A | 3/1974 | |

(Continued)

OTHER PUBLICATIONS

Kramer, John W. et al., "Low Pressure Carbonylation of Epoxides to b-Lactones", Organic Syntheses, vol. 86, 2009, pp. 287-297, XP55782122.
Getzler et al., "Catalytic Carbonylation of B-Lactones to Succinic Anhydrides", Journal of the American Chemical Society, vol. 126, No. 22, 2004, pp. 6842-6843.
Arrizabalaga, Philippe et al., "Intramolecular Influence of a Carboxylic Function on Platinum Blue Synthesis. A Systematic Study of Complexes Originating from Acid Amides." J. Am. Chem. Soc. 1984, 106, 4814-4818 (5 pages).
Naps, Marguerite et al., "Optically Active Mono-substituted Succinic Acids and Derivatives." Journal of the American Chemical Society, vol. 62, 1940, pp. 2450-2457 (8 pages).
Tuman, Walter J et al., "cis-8,9-Dihydroisoxazolo[5,4-d]pyrimidine-4,6(5H,7H)-diones." J. Org. Chem, vol. 37, No. 19, 1972, pp. 2983-2986 (4 pages).

(Continued)

Primary Examiner — Deborah D Carr
(74) Attorney, Agent, or Firm — Young Basile Hanlon & MacFarlane, P.C.

(57) ABSTRACT

The present invention is directed to processes for producing isocyanates and isocyanate derivatives from epoxide and carbon monoxide reagents. In preferred embodiments, the processes include a step for providing carbonylation of an epoxide reagent with a carbon monoxide reagent to produce a beta-lactone intermediate. In certain preferred embodiments, further carbonylation of a beta-lactone intermediate produces a succinic anhydride intermediate. The processes of the present invention include steps for rearranging beta-lactone intermediates and/or succinic anhydride intermediates to produce isocyanate products and/or isocyanate derivatives. In certain preferred embodiments, the isocyanate products may be copolymerized with polyol oligomers to provide polyurethane products.

20 Claims, No Drawings

(56) References Cited

U.S. PATENT DOCUMENTS

| | | | |
|---|---|---|---|
| 2011/0251425 A1* | 10/2011 | Penzel | C07C 263/10 |
| | | | 422/224 |
| 2012/0123137 A1* | 5/2012 | Allen | C07C 67/317 |
| | | | 549/328 |
| 2014/0303377 A1* | 10/2014 | Yoshida | C07C 215/68 |
| | | | 546/261 |
| 2016/0016876 A1 | 1/2016 | Mahoney | |
| 2016/0102068 A1 | 4/2016 | Allen et al. | |
| 2017/0029352 A1 | 2/2017 | Sookraj et al. | |
| 2017/0145126 A1 | 5/2017 | Mahoney | |
| 2017/0267618 A1 | 9/2017 | Sookraj et al. | |
| 2018/0030201 A1 | 2/2018 | Farmer et al. | |
| 2018/0094100 A1 | 4/2018 | Farmer et al. | |
| 2018/0282251 A1 | 10/2018 | Sookraj | |
| 2018/0305286 A1 | 10/2018 | Sookraj | |
| 2019/0002293 A1 | 1/2019 | Sookraj et al. | |
| 2019/0233360 A1 | 8/2019 | Farmer et al. | |
| 2020/0087457 A1 | 3/2020 | Lee et al. | |

FOREIGN PATENT DOCUMENTS

| | | |
|---|---|---|
| JP | S49-092031 A | 9/1974 |
| JP | S49-125332 A | 11/1974 |
| JP | S57-200345 A | 12/1982 |
| JP | S64-500198 A | 1/1989 |
| JP | H01-188512 A | 7/1989 |
| JP | H02-001432 A | 1/1990 |
| JP | H08-027092 A | 1/1996 |
| JP | H09-095464 A | 4/1997 |
| JP | 2000-256300 A | 9/2000 |
| JP | 2000-319627 A | 11/2000 |
| JP | 2001-011038 A | 1/2001 |
| JP | 2002-511445 A | 4/2002 |
| JP | 2005-035982 A | 2/2005 |
| JP | 2005-511753 A | 4/2005 |
| JP | 2005-200406 A | 7/2005 |
| JP | 2006-058546 A | 3/2006 |
| JP | 2007-520486 A | 7/2007 |
| JP | 2008-150322 A | 7/2008 |
| JP | 2011-083288 A | 4/2011 |
| JP | 2013-112666 A | 6/2013 |
| JP | 2014-527456 A | 10/2014 |
| JP | 2015-535020 A | 12/2015 |
| JP | 2017-171681 A | 9/2017 |
| WO | 2013063191 A1 | 5/2013 |
| WO | 2013083724 A1 | 6/2013 |
| WO | 2013122905 A1 | 8/2013 |

OTHER PUBLICATIONS

Yoshimura, Akira et al., "(Tosylimino)phenyl-2-iodane as a Reagent for the Synthesis of Methyl Carbamates via Hofmann Rearrangement of Aromatic and Aliphatic Carboxamides." J. Org. Chem, vol. 77, No. 4, Feb. 9, 2012, pp. 2087-2091) (5 pages).

Partial European Search Report in co-pending Application No. EP22193951.5 dated Oct. 11, 2022 (16 pages).

Office Action from Japanese Patent Office for Application No. 2020-513777 with translation, dated Apr. 6, 2021. (6 pages).

Office Action from Japanese Patent Office for Application No. 2020-513777 with translation, dated Nov. 30, 2021. (6 pages).

Search Report from Japanese Patent Office for Application No. 2020-513777 with translation, dated Mar. 4, 2021. (38 pages).

Succinic acid, the Iwanami great dictionary, 1998, and the 5th group (1998)—p. 485.

Hydroxamic acid, the Iwanami physicochemistry dictionary, 1998, and the 5th group (1998)—p. 254.

Sy*, Anita O., et al., "Synthesis of Aliphatic Isocyanates Via a Two-Phase Hofmann Reaction," Tetrahedrom Letters vol. 21, pp. 2223-2226. Pergamon Press Ltd., 1980. (4 pages).

Notification of First Office Action in co-pending application CN201880064963.4 dated Jul. 14, 2022 (with English translation) (18 pages).

International Search Report for co-pending International Application No. PCT/US2018/054375 dated Dec. 14, 2018 (2 pages).

Written Opinion of the International Searching Authority for co-pending International Application No. PCT/US2018/054375 dated Dec. 14, 2018 (6 pages).

Gresham, T.L. et al., "ß-Propiolactone. XI. Reactions with Ammonia and Amines." Contribution from the B.F. Goodrich Research Center, Jul. 1951. 4 pages.

Kramer, John W. et al. Practical ß-Lactone synthesis: Epoxide Carbonylation at 1 atm. Organic Letters 2006 vol. 8, No. 17, 3709-3712. May 26, 2006. Four pages.

Pini, Dario et al., The Absolute Stereochemistry at C1 and C2 of Cis-(+)-2-Hydroxy-2-phenylcyclohexanecarboxylic Acid (Cicloxilic Acid), Tetrahedron vol. 50, No. 1, pp. 205-216, 1994. 12 pages.

Supplementary Partial European Search Report in co-pending application EP18864727 (Date of Completion of search: Mar. 19, 2021). 21 pages.

Sy, Anita O. et al. "Synthesis of Aliphatic Isocynates via a Two-Phase Hofmann Reaction", Tetrahedron Letters vol. 21, pp. 2223-2226. Pergamon Press Ltd. 1980. 4 pages.

Yoganathan, Sabesan et al., "N-Methylimidazole-catalyzed Synthesis of Carbamates from Hydroxamic Acids via the Lossen Rearrangement", Organic Letters 2013, vol. 15, No. 3 602-605, received Dec. 14, 2012. 4 pages.

* cited by examiner

ISOCYANATES, DERIVATIVES, AND PROCESSES FOR PRODUCING THE SAME

CROSS-REFERENCE TO RELATED APPLICATIONS

This application is a national filing under 35 USC 371 of the PCT Application PCT/US2018/054375 filed Oct. 4, 2018, published as WO2019/070981, which claims priority from provisional application U.S. 62/568,511 filed Oct. 5, 2017 and provisional application U.S. 62/661,951 filed Apr. 24, 2018, all incorporated herein by reference in their entirety for all purposes. This application claims priority from these provisional applications.

FIELD OF DISCLOSURE

The present invention relates to processes for producing isocyanates and isocyanate derivatives, and more particularly, the processes for producing isocyanates and isocyanate derivatives from epoxide and carbon monoxide reagents which may be comprised of atoms from biological, recycled, renewable, or otherwise sustainable raw material sources to produce environmentally friendly alternatives to materials used for coatings, adhesives, sealants, and elastomers.

BACKGROUND

Carbonylation generally describes a reaction that introduces a carbon monoxide group into an organic or inorganic molecule. A carbonylation reaction may be used to produce a beta-lactone from an epoxide.

Beta-lactones are a class of organic molecules generally comprising a strained four-membered heterocyclic ring. Intrinsic ring strain causes beta-lactones to undergo nucleophilic ring-opening reactions. Beta-lactones are useful building blocks as monomers in both hetero-polymers and homo-polymers. Further, beta-lactones may act as a structural framework for certain natural and synthetic bioactive molecules.

An isocyanate is an organic compound that has a functional group with the formula R—N=C=O. Conventional processes produce isocyanates by reacting an amine reagent with phosgene via a carbamoyl chloride intermediate. Due to the hazards associated with phosgene, the production of isocyanates requires special precautions.

An isocyanate that has two or more isocyanate groups is known as a diisocyanate or polyisocyanate. Diisocyanates and polyisocyanates are characterized by terminal isocyanate groups, which may react with nucleophiles. Diisocyanates and polyisocyanates are generally manufactured for reactions with the hydroxyl groups of polyols in the production of polyurethanes.

There exists a need for highly customizable processes for producing isocyanates and isocyanate derivatives including polyurethanes.

SUMMARY

The present invention is directed to processes for producing isocyanates and isocyanate derivatives from epoxide and carbon monoxide reagents. Preferred embodiments produce intermediate molecules which may be rearranged to produce the isocyanates and isocyanate derivatives. The processes of the present invention include steps directed to the Schmidt reaction, Hofmann rearrangement, Curtius rearrangement, and Lossen rearrangement to produce isocyanate products.

In certain preferred embodiments, diisocyanates and/or polyisocyanates may be copolymerized with polyols comprised of epoxide and carbon monoxide reagents to produce polyurethane products. The polyurethanes of the present invention may be used to manufacture a broad spectrum of materials including flexible foam, rigid foam such as for insulation panels, microcellular foam for seals and gaskets, durable elastomers such as for wheels and tires, high performance adhesives, surface coatings and sealants.

One object of the present invention is to provide process versatility through series of alternative chemical pathways to produce isocyanate products and derivatives from epoxide reagents and carbon monoxide reagents. Advantageously, the processes of the present invention provide for more cost-efficient use of raw materials, equipment, and facilities.

Another object of the present invention is to provide for environmentally responsible production of isocyanate and isocyanate derivatives through use of reagents having high bio-based content. Advantageously, the processes of the present invention may provide a decreased carbon footprint. The processes of the present invention have cost and carbon efficiency advantages relative to other conventional processes for isocyanate production processes. The processes provide flexibility to modulate the bio-content of the product.

Yet another object of the present invention is to produce bio-based isocyanate, isocyanate derivative, and polyurethane products useful for applications as coatings, adhesives, sealants, and/or elastomers. Preferred embodiments of the present invention may produce products applied as coatings to improve the appearance and lifespan of manufactured goods. Preferred embodiments of the present invention may produce products applied as adhesives and/or sealants to provide strong bonding or tight seals for a variety of manufactured goods. Preferred embodiments of the present invention may produce products applied as elastomers sized, shaped, and configured into a variety of manufactured goods.

While this disclosure is susceptible to various modifications and alternative forms, specific exemplary embodiments have been shown by way of example in the drawings and described in detail. There is no intent to limit the disclosure to the specific exemplary embodiments disclosed. The intention is to cover all modifications, equivalents, and alternatives falling within the scope of the disclosure as defined by the appended claims.

DETAILED DESCRIPTION OF EMBODIMENTS

The following description includes embodiments which are directed to processes for producing isocyanates and isocyanate derivatives from epoxide and carbon monoxide reagents. It should be recognized, however, that such description is not intended as a limitation on the scope of the present disclosure but is instead intended to provided as a description of exemplary aspects.

Renewable sources means a source of carbon and/or hydrogen obtained from biological life forms that can replenish itself in less than one hundred years.

Renewable carbon means carbon obtained from biological life forms that can replenish itself in less than one hundred years.

Recycled sources mean carbon and/or hydrogen recovered from a previous use in a manufactured article.

Recycled carbon means carbon recovered from a previous use in a manufactured article.

Biodegradability and biodegradable refers to the ability of a material to be broken down (decomposed) rapidly by the action of living organisms such as bacteria, fungi, microorganisms or other biological means wherein "rapidly" is typically less than 10 years, 5 years, or 2 years.

Sustainable material and sustainable polymer means a biodegradable material and polymer, respectively, that is derived at least in part from sources with bio-content and has a bio-content equal to a minimum of 10%, and more typically 20%, 50%, 75%, 90%, 95%, or 100% of the total amount of carbon and hydrogen in the material. The term bio-content means biogenic carbon also known as bio-mass derived carbon, carbon waste streams, and carbon from municipal solid waste. In some variations, bio-content can be determined based on the following:

Bio-content or Bio-based content=[Bio (Organic) Carbon]/[Total (Organic) Carbon] 100%, as determined by ASTM D6866 (Standard Test Methods for Determining the Bio-based (biogenic) Content of Solid, Liquid, and Gaseous Samples Using Radiocarbon Analysis).

As used herein, the term "about" preceding one or more numerical values means the numerical value ±5%. It should be understood that reference to "about" a value or parameter herein includes (and describes) aspects that are directed to that value or parameter per se. For example, description referring to "about x" includes description of "x" per se.

Further, it should be understood that reference to "between" two values or parameters herein includes (and describes) aspects that include those two values or parameters per se. For example, description referring to "between x and y" includes description of "x" and "y" per se.

Embodiments

Preferred embodiments are directed to processes for producing isocyanates and isocyanate derivatives from epoxide and carbon monoxide reagents. Beta-lactone intermediates may be produced from carbonylation of an epoxide with carbon monoxide. The epoxide sources and carbon monoxide sources may have a bio-based carbon content. In certain embodiments, it is preferable that epoxide sources and carbon monoxide sources have a high bio-based carbon content. In certain preferred embodiments, at least a portion of the beta-lactone intermediate is produced by the carbonylation of an epoxide having a bio-based carbon content of at least 10% with carbon monoxide that has a bio-based carbon content of at least 10%. In some embodiments, the epoxide is ethylene oxide.

In certain embodiments, carbonylation may utilize a metal carbonyl-Lewis acid moiety such as those described in U.S. Pat. No. 6,852,865. In certain embodiments, carbonylation includes the carbonylation catalysts disclosed in U.S. patent application Ser. Nos. 10/820,958; and 10/586,826. In certain embodiments, carbonylation includes the catalysts disclosed in U.S. Pat. Nos. 5,310,948; 7,420,064; and 5,359,081. The entirety of each of the preceding references is incorporated herein by reference.

In certain preferred embodiments, the processes of the present invention provide for carbonylation of epoxide using catalysts, systems, and methods described in U.S. Pat. No. 9,327,280, herein incorporated by reference. Carboxylation of an epoxide with carbon monoxide to produce a beta-lactone proceeds according to the following general reaction:

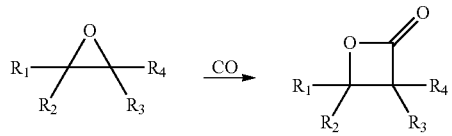

Table 1 illustrated below includes Column A directed to a non-exhaustive list of epoxides which may undergo carbonylation to produce beta-lactone according to the processes of the present invention and Column B directed to a non-exhaustive list of beta-lactones which may be produced according to the present invention.

TABLE 1

| Column A | Column B |
|---|---|
| ethylene oxide | β-propiolactone |
| propylene oxide | β-butyrolactone or/and β-butyrolactone (isomer) |
| epichlorohydrin | 4-(chloromethyl)-β-propiolactone |

TABLE 1-continued
| Column A | Column B |
|---|---|
| 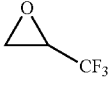 | 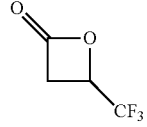 |
| 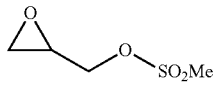 | 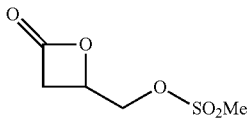 |
| 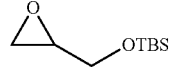 | 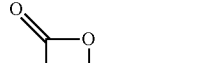 |
| 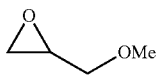 | 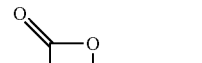 |
|  | 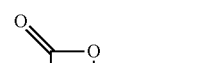 |
| 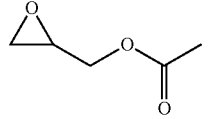 | 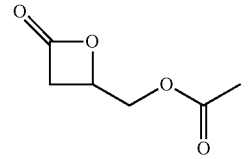 |
| 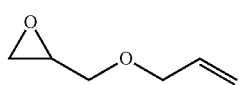 | 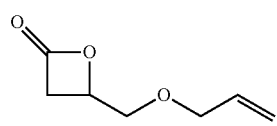 |
| 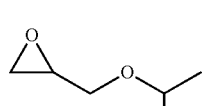 | 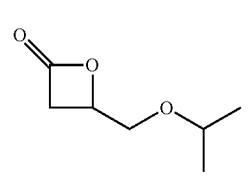 |
| 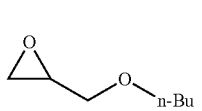 | 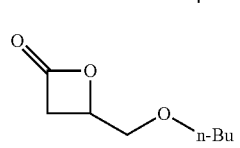 |
| 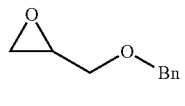 | 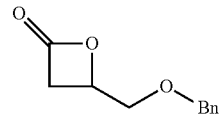 |
| 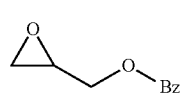 | 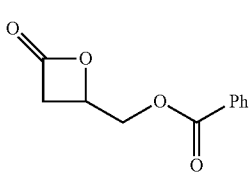 [SMILES: O=C1CC(COC(=O)c2ccccc2)O1] |

TABLE 1-continued
| Column A | Column B |
|---|---|
| 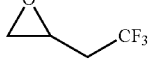 | 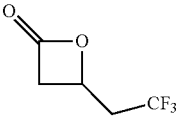 |
| 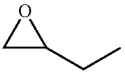 | 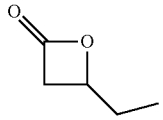 |
| 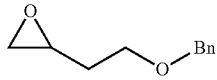 |  |
| 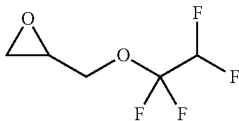 [SMILES: FC(F)C(F)(F)OCC1CO1] | 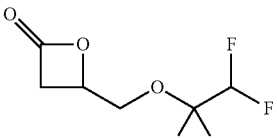 |
| 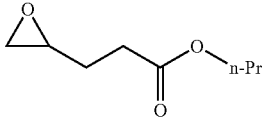 | 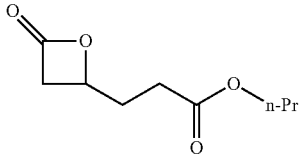 |
| 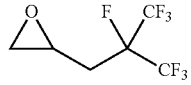 | 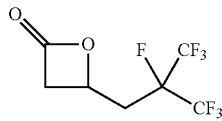 |
| 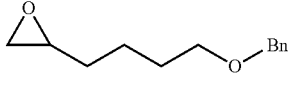 | 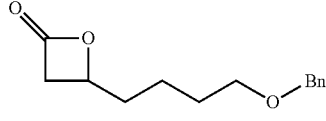 [SMILES: O=C1CC(CCCCOCc2ccccc2)O1] |
| 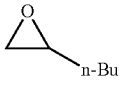 | 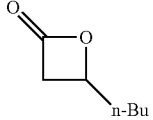 |
| 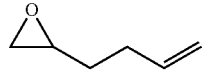 | 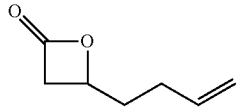 |
| 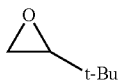 | 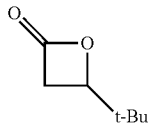 |
| 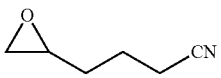 | 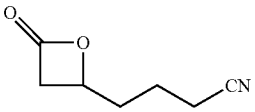 |

TABLE 1-continued
| Column A | Column B |
|---|---|
| 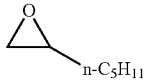 | 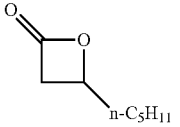 |
| 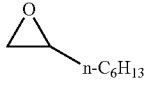 | 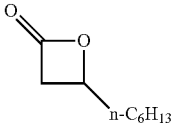 |
| 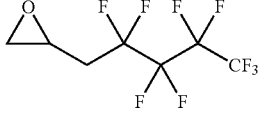 [SMILES: FC(F)(F)C(F)(F)C(F)(F)C(F)(F)CC1CO1] | 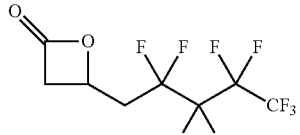 |
| 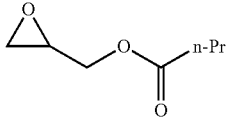 | 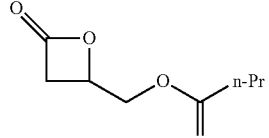 |
| 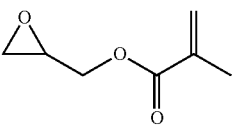 | 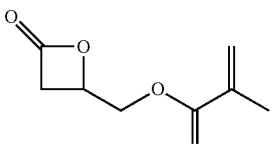 |
| 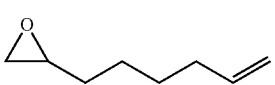 |  |
| 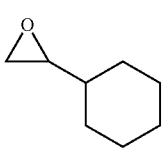 | 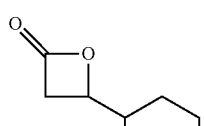 |
|  | 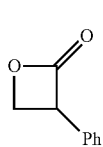 [SMILES: O=C1OCC1c1ccccc1] |
| 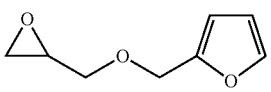 |  |
| 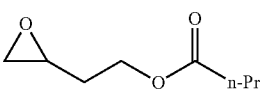 | 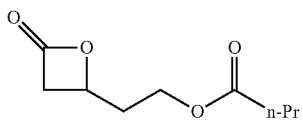 |

TABLE 1-continued

| Column A | Column B |
|---|---|
| (structures) | (structures) |

TABLE 1-continued

| Column A | Column B |
|---|---|
| | |

TABLE 1-continued
| Column A | Column B |
|---|---|
| 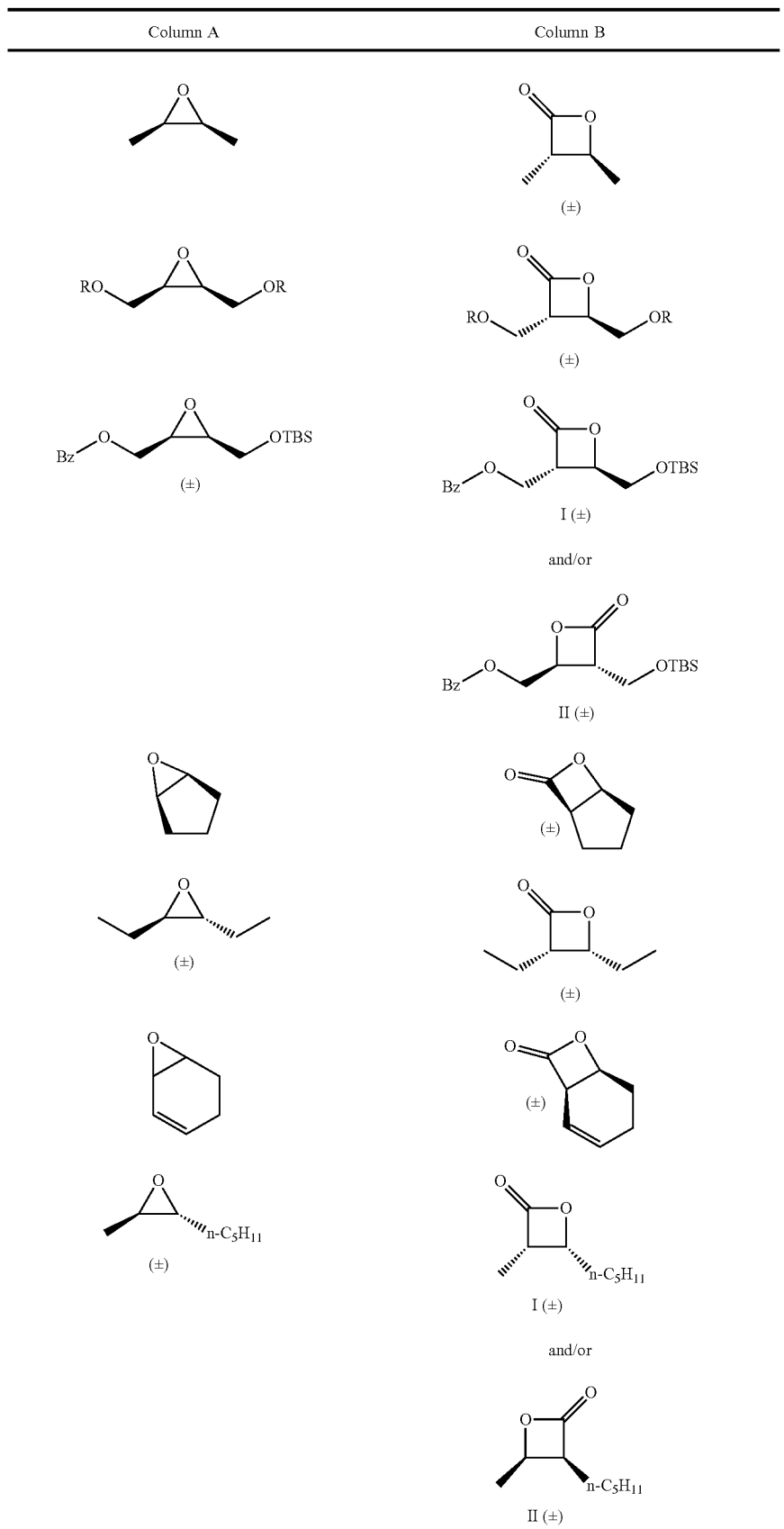 | |

TABLE 1-continued
| Column A | Column B |
|---|---|
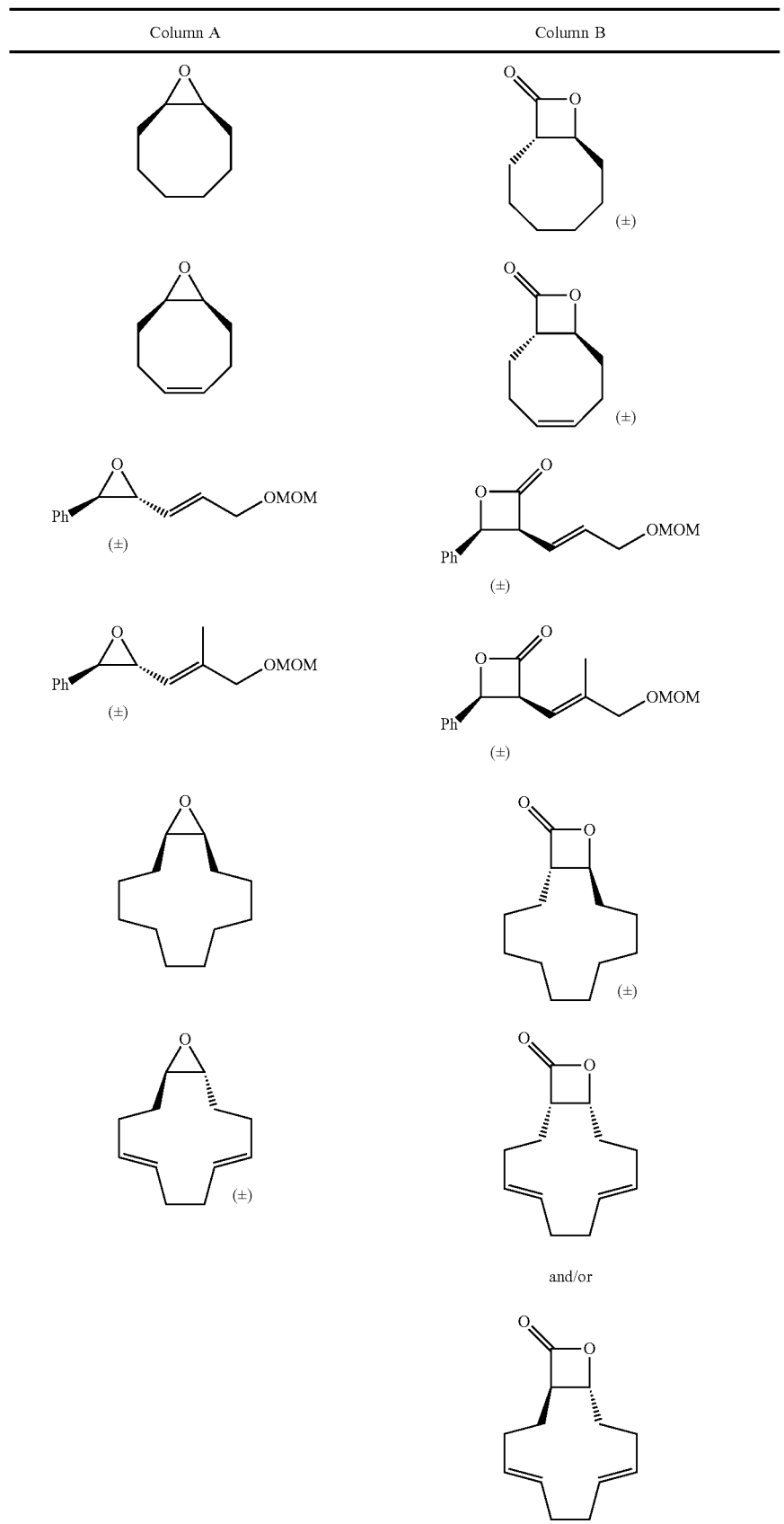

TABLE 1-continued

| Column A | Column B |
|---|---|
| 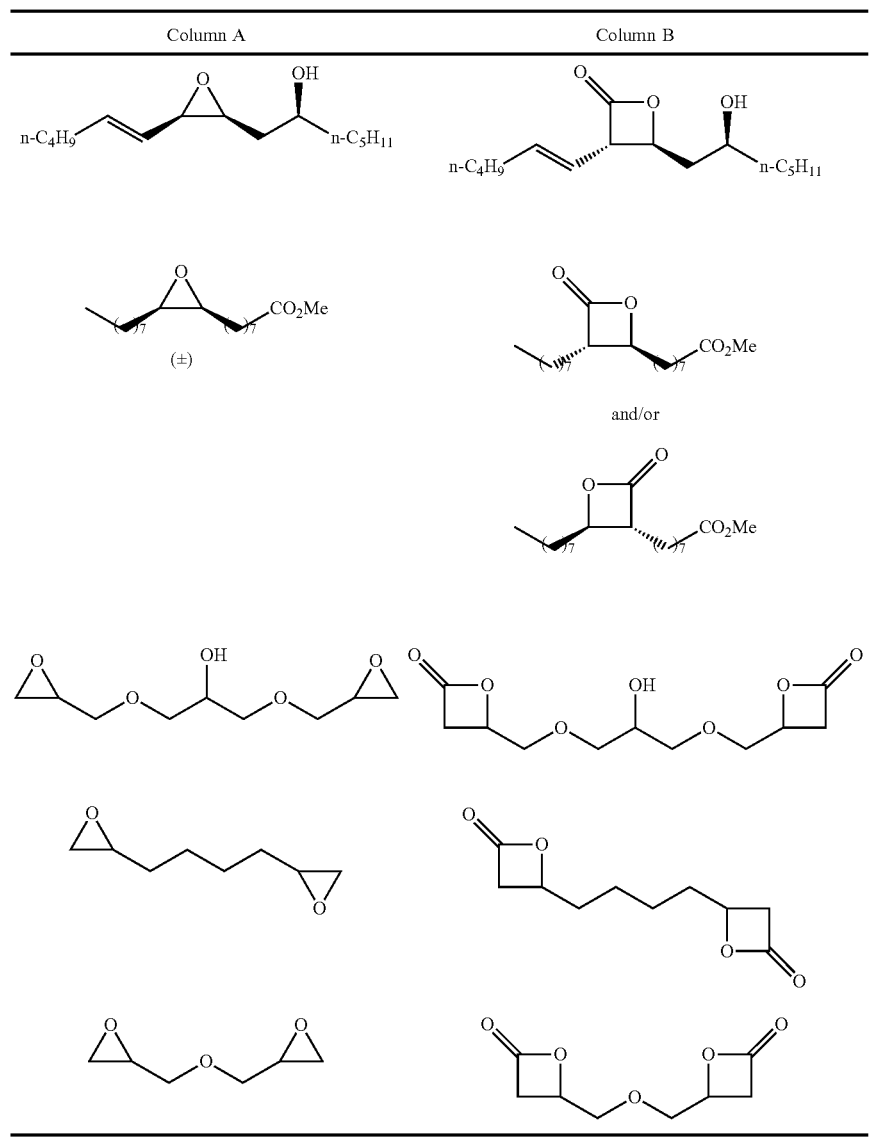 | |

The processes may cause a beta-lactone intermediate to undergo an oxygen-alkyl or oxygen-acyl bond cleavage in the presence of a nucleophile. In certain preferred embodiments, the processes include a step for reacting a beta-lactone intermediate with a nucleophile to produce a ring-opened intermediate with the following general structure:

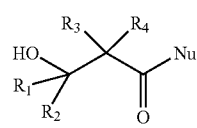

In certain embodiments having the step for reacting a beta-lactone intermediate with a nucleophile, the nucleophile may be ammonia. The ring-opened intermediate produced by reacting the beta-lactone intermediate with ammonia is an amide. Reacting a beta-lactone intermediate with ammonia to produce an amide ring-opened intermediate may proceed according to the following general reaction:

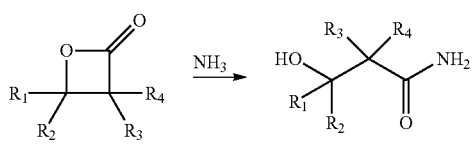

In certain embodiments, the processes include a step for converting an amide ring-opened intermediate to an isocyanate via a process generally known as a Hofmann rearrangement. In certain embodiments, the Hofmann rearrangement involves the reaction of a halogen reagent with a caustic base reagent in the presence of the amide ring-opened intermediate. For example, a bromine reagent may react with a sodium hydroxide reagent to form sodium hypobromite in situ, which reacts with the amide ring-opened intermediate to produce an isocyanate product. The isocyanate product produced according to the Hofmann rearrangement generally proceeds as follows:

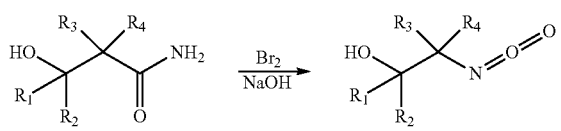

In certain embodiments having the step for reacting a beta-lactone intermediate with a nucleophile, the nucleophile may be a hydroxylamine. The ring-opened intermediate produced by reacting the beta-lactone intermediate with hydroxylamine is a hydroxamic acid. Reacting a beta-lactone intermediate with the hydroxylamine to produce a hydroxamic acid ring-opened intermediate may proceed according to the following general reaction:

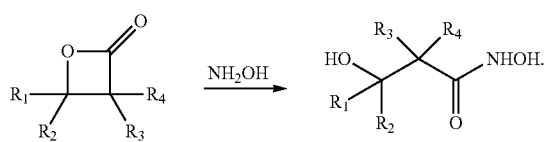

In certain embodiments, the processes include a step for converting a hydroxamic acid ring-opened intermediate to an isocyanate via a process generally known as a Lossen rearrangement. In certain embodiments, the Lossen rearrangement involves formation of an O-acyl, sulfonyl, or phosphoryl intermediate hydroxamic acid 0-derivative and then conversion to its conjugate base. For example, 4-toluenesulfonyl chloride may be used to form a sulfonyl ortho-derivative of the hydroxamic acid intermediate to produce an isocyanate product. The isocyanate product produced according to the Lossen rearrangement generally proceeds as follows:

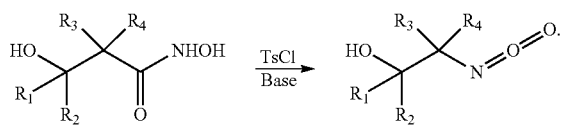

In certain preferred embodiments, the processes include a step for rearranging a beta-lactone intermediate to produce an organic acid intermediate, such as acrylic acid, similar to the systems and processes disclosed in U.S. patent application Ser. No. 15/640,197, herein incorporated by reference. In certain embodiments, the processes include a step for contacting the beta-lactone intermediate with a catalyst to produce an organic acid. In some embodiments, the catalyst includes a zeolite. In some variations, the zeolite is an acidic zeolite, metal oxide, supported acid such as phosphoric acid (solid phosphoric acid—SPA), or heteropolyacid. The step for rearranging the beta-propiolactone to produce the organic acid can be performed in fixed bed or fluidized bed continuous reactor. Optionally, the beta-lactone can be diluted with an inert solvent or inert gas prior to being fed to the conversion reactor. Such processes may produce organic acid products in high yields, by minimizing other by-products that may form, such as polylactones and polyorganic acids.

In certain embodiments, the processes may include a step for producing an organic acid intermediate by thermolysis of a polylactone intermediate similar to the systems and processes disclosed in U.S. patent application Ser. No. 15/494,805, herein incorporated by reference. A polylactone intermediate may be formed by ring-opening polymerization a beta-lactone intermediate using a polymerization initiator similar to the systems and processes disclosed in U.S. patent application Ser. No. 15/369,764, herein incorporated by reference.

Embodiments including a step for contacting beta-lactone intermediate with a catalyst to produce and organic acid may be performed using certain reactor configurations including a continuous fixed-bed reactor operating under reduced pressure (under vacuum) and undiluted beta-lactone is vaporized prior to entering the reactor; a continuous fixed-bed reactor and beta-lactone is vaporized and diluted with inert gas (such as nitrogen) prior to entering the reactor, and; a fluidized bed reactor and beta-lactone together with inert gas (such as nitrogen) is fed into the reaction zone where the catalyst is suspended/fluidized in the flow of gas. In some embodiments, the beta-lactone intermediate can be diluted in a solvent. The conversion of beta-lactone to organic acid may be conducted in the temperature range from 100° C. to 300° C., preferably from 150° C. to 250° C.

In certain preferred embodiments including an organic acid intermediate, the processes may include a step for combining the organic acid intermediate with an azide reagent to produce an isocyanate product via a Schmidt reaction. The Schmidt reaction includes the formation of an acylium ion by protonation and loss of water. Reaction with hydrazoic acid forms the protonated azido ketone, which goes through a rearrangement reaction with the alkyl group, migrating over the carbon-nitrogen bond, losing nitrogen. By removing water from the reaction system, the isocyanate product may not convert to a carbamate. In some embodiments, water may convert a protonated isocyanate product to a carbamate derivative. Processes including the step for rearranging a beta-lactone intermediate to produce and organic acid intermediate and the step for combining the organic acid intermediate with an azide reagent to produce an isocyanate product via a Schmidt reaction generally proceeds as follows:

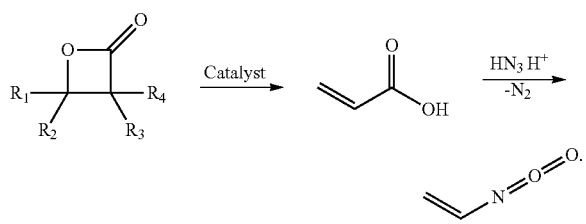

In certain preferred embodiments including an organic acid intermediate, the processes may include a step for converting the organic acid to an acyl azide intermediate. The acyl azide intermediate may be formed from the reaction of acid chlorides or anhydrides with sodium azide or trimethylsilyl azide. The acyl azide intermediate may also be formed by treating acylhydrazines with nitrous acid. Also, the acyl azide intermediate may be formed by the direct reaction of the organic acid intermediate acid with diphenylphosphoryl azide. The step for converting the organic acid to an acyl azide intermediate generally may proceed as follows:

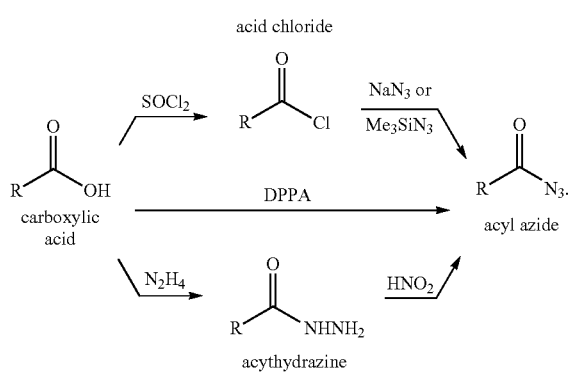

In certain preferred embodiments including an acyl azide intermediate, the acyl azide intermediate may be converted to an isocyanate product via Curtius rearrangement with thermal decomposition and loss of nitrogen gas.

In certain preferred embodiments, the beta-lactone intermediate may undergo carbonylation to form a succinic anhydride intermediate using a method previously disclosed and incorporated by reference. In certain embodiments, the processes of the present invention may include a step for combining the succinic anhydride intermediate with a nucleophile to produce an amide intermediate. In some embodiments, the nucleophile may be ammonia and the amide intermediate may be formed according to the processes as follows:

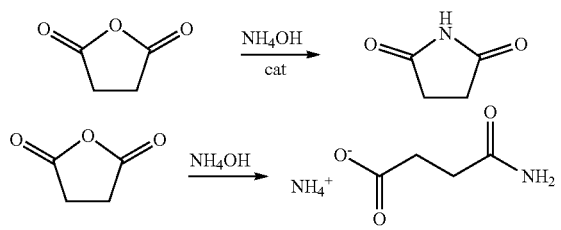

In certain embodiments, the amide intermediate formed from succinic anhydride may be converted to an isocyanate or a diisocyanate. In some embodiments, the amide intermediate formed from succinic anhydride may undergo Hofmann rearrangement to form an isocyanate or a diisocyanate.

In certain embodiments, the succinic anhydride intermediate may be converted to a diamide intermediate. In some embodiments, the diamide intermediate is a succinamide. In one embodiment, the diamide intermediate may be formed according to the process as follows:

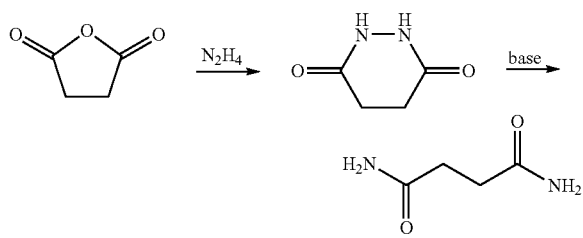

In certain embodiments, the succinic anhydride intermediate may be converted to dimethyl adipate wherein the dimethyl adipate may then be converted to adipic acid dihydrazide (ADH). The ADH intermediate may undergo Curtius rearrangement to form an isocyanate. In a preferred embodiment, the ADH intermediate is fully converted wherein each terminal end is an isocyanate forming a diisocyanate. In certain embodiments, other intermediary compositions such as beta-propiolactone may be further reacted with functional groups to obtain different diisocyanates and isomers. In one embodiment, the diisocyanate formed is 1,4-Diisocyanatobutane (also known as butane diisocyanate or BDI). In one embodiment, the diisocyanate may be formed according to the process as follows:

Curtius Rearrangement

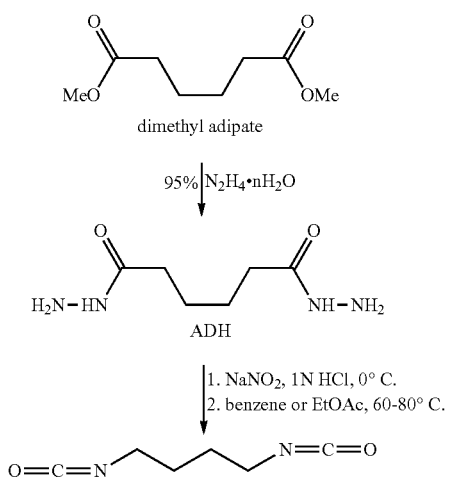

OK-61, 5 g batch, 3.0 g, 75%;
OK-62, 10 g batch, 5.3 g, 66%;
OK-64, 10 g batch, 5.4 g, 67%;
OK-65, 100 g batch, 33.6 g, 42%;
OK-68, 25 g batch, 12.1 g, 60%;
OK-68-2, 25 g batch, 16.0 g, 79%;

In one embodiment, hydrazine hydrate is used to convert dimethyl adipate to ADH. In another embodiment, the composition of hydrazine hydrate is 95%. In another embodiment, 372 ml of an 82% composition of hydrazine hydrate is mixed with 200 ml of 0.006M dimethyl adipate and stirred for 72 hours at room temperature resulting ADH (200 g, 94%) to be used without further purification.

In one embodiment, nitrous acid is created using sodium nitrite and hydrochloric acid, wherein the nitrous acid is used in combination with benzene or ethyl acetate in the conversion of ADH to a diisocyanate. In one embodiment, the nitrous acid is at 0° C., and the benzene or ethyl acetate is within the range of 60° C.-80° C.

In one embodiment, 25 g of 0.144 mol ADH was dissolved in 288 ml of 1N aqueous hydrochloric acid. Upon chilling the solution to a temperature no less than 0° C. and no greater than 5° C. in an ice-salt bath, a solution of 25 g (0.362 mol) of sodium nitrite in 40 ml of Q-water was added with stirring at a rate wherein the temperature of the solution did not exceed 8° C. Thereinafter, 100 ml of benzene was added to the solution. Upon completion, the benzene layer was separated and the aqueous layer was extracted using 500 ml of benzene (250 ml at each extraction). The extracts were combined and dried for 2 hours over anhydrous calcium chloride. While stirring, the benzene layer was heated at 64° C. to decompose the diazide formed until no further nitrogen was evolved. The benzene was then removed under vacuum, wherein the residual was collected for 30 min at 40 mbar at 82° C.

In one embodiment, upon completion of thermal decomposition of the Curtius rearrangement, the minimum isolation yields of diisocyanate material is no less than 42%. In another embodiment, upon completion of thermal decomposition of the Curtius rearrangement, the minimum isolation yields of diisocyanate material was no more than 79%. Although distillation may be used to purify the diisocyanate, the diisocyanate generally does not require further purification and can be directly used for condensation with polyols to produce polyurethane foams.

In another embodiment, the succinic anhydride intermediate may be converted to dimethyl adipate wherein hydroxylamine hydrate is used in to convert dimethyl adipate to dihydroxymic diacid. Through thermal decomposition of the Lossen arrangement, diisocyanate is produced.

In one embodiment, the diisocyanate may be formed according to the process as follows:

Lossen Rearrangement

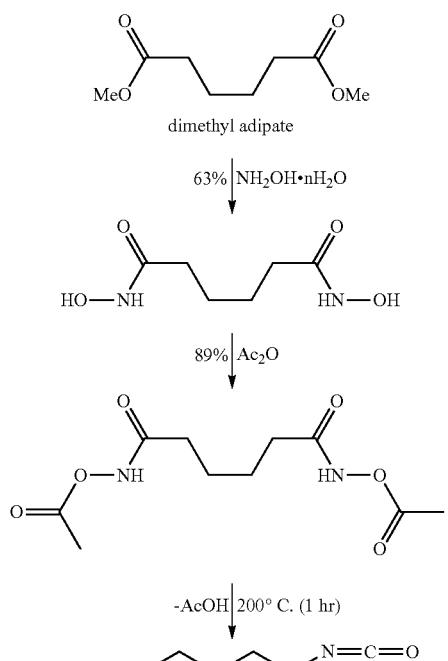

~2% (contaminated product), ~3 mg

In another embodiment, the composition of hydroxylamine hydrate is 63%. In another embodiment, the dihydroxymic diacid is converted to a diisocyanate via the Lossen rearrangement at a temperature of about 200° C. Table 2 below represents a summary of experiment conditions used to obtain tetramethylene diisocyanate thru the Lossen rearrangement.

TABLE 2

Thermal degregation of O-acetylated dihydroxamic diacid to BDI

| Experiment | Coolant | Vacuum | Duration (min) | Temperature (° C.) |
|---|---|---|---|---|
| 1 | Acetone/Dry Ice | Water aspirator | 60 | 200 |
| 2 | Ice bath | Water aspirator | 15 | 180 |
| 3 | Acetone/Dry Ice | Water aspirator | 30 | 200 |
| 4 | Acetone/Dry Ice | Schlenk line | 180 | 200 |
| 5 | i-propanol/Dry ice | Water aspirator | 30 | 200 |

In another embodiment 100 mL of aqueous hydroxylamine hydrate at the composition of 50% was mixed with 100 mL of 0.610 mol of dimethyl adipate in 200 mL of methanol. The resulting solution was agitated for 72 hours at room temperature resulting in solid adipohydroxamic acid. The adipohydroxamic acid was filtered off and washed with cold methanol and dried under a vacuum overnight resulting in 67.238 g (63% yield). The percent yield is based upon the starting materials and mass balance.

In another embodiment, the synthesis of acetylated adiphydroxamic acid (also known as hexanedihydroxamic acid) was procured with 5 g (0.028 mol) of hexanedihydroxamic acid which is mixed with 40 mL (0.426 mol) acetic anhydride and stirred at room temperature for two days under nitrogen. After two days, the reaction mixture was filtered and the product was obtained as a white solid via cold methanol wash and dried under a vacuum resulting in 6.552 g (89% yield).

In another embodiment, the Lossen rearrangement was performed by adding 0.5 g (0.002 mol) of 0-acetyl hexanedihydroxamic acid into a sublimation apparatus and heated at 200° C. for 30 minutes. Dry ice and isopropanol were used as a coolant to condense reaction products under a water aspirator vacuum. The resulting BDI was collected at 0.005 g (2% yield).

In certain embodiments, the diamide intermediate formed from succinic anhydride may be converted to a diisocyanate by any of the processes described herein.

In certain embodiments, succinic anhydride is hydrolyzed as depicted in the scheme below to afford succinic acid. Succinic acid may then be converted to succinamide, for example, by first converting succinic acid to a corresponding diester, i.e. dimethyl or diethyl succinate, and then treating the succinate with ammonia to produce succinamide. In certain embodiments, the diamide intermediate formed from succinic anhydride may be converted to a diisocyanate by any of the processes described herein.

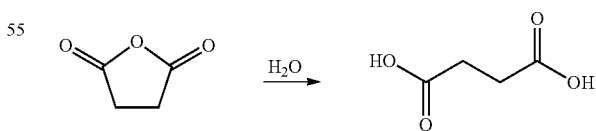

In certain preferred embodiments, the processes include steps for producing aromatic isocyanates. In certain embodiments including steps for producing aromatic isocyanates, a beta-lactone intermediate may undergo carbonylation to produce a succinic anhydride intermediate. The succinic anhydride intermediate may be oxidized to provide an unsaturated four carbon intermediate selected from the group consisting of: maleic anhydride, maleic acid, fumaric acid, a mono- or di-ester of fumaric acid, a mono- or di-ester of maleic acid, a mono- or bis-salt of fumaric acid, a mono- or bis-salt of maleic acid, and a mixture of any two or more of these similar to the system and processes disclosed in U.S. Pat. No. 9,719,037, herein incorporated by reference. The unsaturated four carbon intermediate may then be contacted with furan to provide a cyclohexene ring intermediate. In certain embodiments, the processes include the step of dehydrating the cyclohexene ring intermediate to form a disubstituted benzene ring intermediate. In certain embodiments, the disubstituted benzene ring intermediate is selected from the group consisting of phthalic anhydride, phthalic acid, a mono- or diester of phthalic acid, a mono- or bis-salt of phthalic acid, and a mixture of two or more of these.

In certain embodiments, the processes may include a step for heating a furan and an unsaturated four carbon intermediate to produce a cyclohexene ring intermediate in a cycloaddition reaction.

In certain embodiments, the cycloaddition reaction is conducted by flowing a mixture of the furan and the unsaturated four carbon intermediate through a heated plug flow reactor in a solvent in the absence of a catalyst. In certain embodiments, the mixture of unsaturated compound and furan is heated to a temperature between 50° C. and 300° C. In certain embodiments, the mixture is heated to a temperature between 50° C. and 150° C., between 100° C. and 200° C., between 120° C. and 180° C. or between 150° C. and 220. ° C. In certain embodiments, the step of heating the mixture of the furan and the unsaturated four carbon intermediate comprises flowing the mixture through a heated plug flow reactor. In certain embodiments, unreacted furan and/or unsaturated four carbon intermediates are present in the outlet of the heated reactor. In certain embodiments, unreacted products present in the outlet of the reactor are separated from the cyclohexene ring intermediate and recycled for further reaction.

In certain preferred embodiments, the cyclohexene ring intermediate and/or the disubstituted benzene ring intermediate may be converted to an aromatic isocyanate product through a Schmidt reaction.

In certain preferred embodiments, the processes of the present invention provide for bio-based pathways to an aromatic dicarboxylic acid, such as terephthalic acid, from bio-based epoxide and carbon monoxide reagents.

Certain embodiments of the processes include production of an aromatic dicarboxylic acid intermediate from a reaction of furan with a beta-lactone intermediate similar to the systems and processes of U.S. Pat. No. 9,718,755, herein incorporated by reference. In certain embodiments, the processes operate in a continuous flow configuration by passing a mixture of furan (or a derivative thereof) and beta-lactone intermediate through a reaction zone, optionally in the presence of solvent, catalysts, or co-reactants. The production of an aromatic dicarboxylic acid intermediate from a reaction of furan with a beta-lactone intermediate may generally proceed as follows:

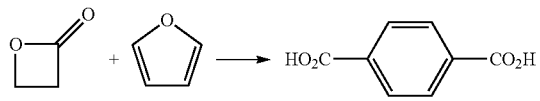

Certain embodiments of the processes include the production of a p-Toluic acid intermediate from bio-based epoxide, carbon monoxide and isoprene reagents. The processes include a step for carbonylation of an epoxide reagent with a carbon monoxide reagent to produce a beta-lactone intermediate. The processes include a step for rearranging a beta-lactone intermediate to produce an organic acid intermediate, such as acrylic acid. The processes of the present invention may include a Diels-Alder reaction of the organic acid intermediate with the isoprene reagent to produce a cyclohexene carboxylic acid intermediate generally proceeding as follows:

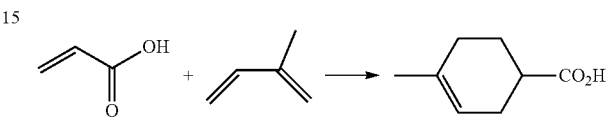

The processes may include steps for dehydro-aromatization of a cyclohexene-carboxylic acid intermediate, such as using sulfuric acid, to produce an aromatic carboxylic acid intermediate, such as p-Toluic acid. The processes for dehydro-aromatization disclosed in Fei Wang et al., Dehydro-aromatization of cyclohexene-carboxylic acids by sulfuric acid: critical route for bio-based terephthalic acid synthesis, Royal Society of Chemistry, 2014, are incorporated by reference. In certain embodiments, the aromatic carboxylic acid intermediate may undergo aerobic oxidation to produce an aromatic dicarboxylic acid intermediate, such as through the processes described in U.S. Pat. No. 3,678,106, herein incorporated by reference. In some embodiments, the dicarboxylic acid intermediate is terephthalic acid.

In certain embodiments, the aromatic dicarboxylic acid intermediate may be reacted with an acyl chloride having the general formula R—COCl to produce a chlorocarbonyl intermediate generally proceeding as follows:

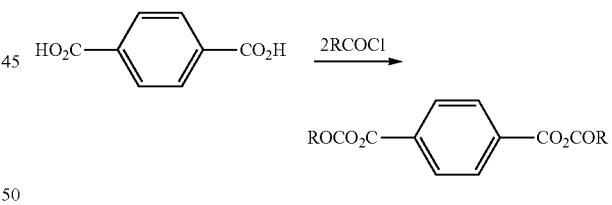

The chlorocarbonyl intermediate may be reacted with hydroxylamine to produce an aromatic hydroxamic acid intermediate generally proceeding as follows:

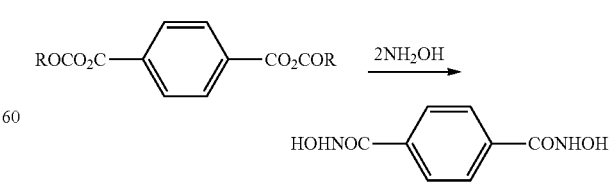

The aromatic hydroxamic acid intermediate may undergo Lossen rearrangement to produce an aromatic isocyanate product proceeding generally as follows:

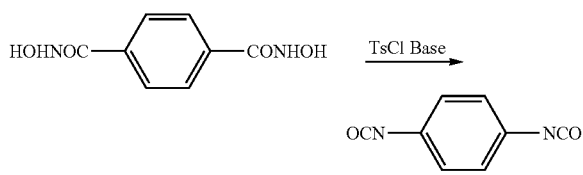

In one embodiment, the process includes a step for adding terephthalamide as a slurry in chloroform into the sublimation reactor, wherein the terephthalamide sublimates under reduced (vacuous) pressure at about 190° C. The isocyanate deposits on a water cooled condenser located within the sublimation apparatus and can be recovered by reflux with chloroform. Acetic acid formed during the sublimation process is removed from the sublimation reactor by vacuum.

In preferred embodiments, the processes include a step for producing a derivative of an isocyanate product. In certain preferred embodiments, the processes may include a step for contacting an isocyanate product with nucleophile. In certain embodiments, the isocyanate product may be contacted with an alcohol nucleophile to produce a carbamate product. In some embodiments, the isocyanate product may be contacted with a water nucleophile to produce a primary amine product. In other embodiments, the isocyanate product may be contacted with an amine nucleophile to produce a urea derivative product. Processes of the present invention including a step for contacting an isocyanate with a nucleophile may generally proceed as follows:

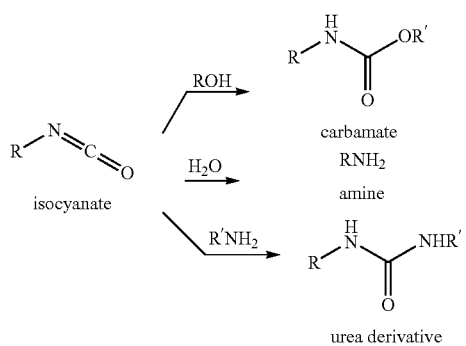

Preferred embodiments of the processes provide for the production of isocyanate derivatives useful in coatings, adhesives, sealants and elastomers. In certain embodiments, the processes may produce a carbamate isocyanate derivative used in production of carbofuran, carbaryl, aldicarb, ethienocarb, fenobucarb, oxamyl, and methomyl insecticides to name a few. In certain embodiments, the processes may produce a urea isocyanate derivative used in production.

In preferred embodiments, the processes of the present invention include a step for copolymerizing an isocyanate product with a polyol to form a polyurethane product. In certain preferred embodiments, a polyol oligomer containing two or more hydroxyl groups may be copolymerized with a diisocyanate or polyisocyanate. In certain embodiments, a diisocyanate or polyisocyanate may be used as a crosslinking agent.

The properties of a polyurethane product may be influenced by the type of isocyanate and polyol monomers. For example, longer polyol oligomers will provide more elasticity and/or flexibility to the polyurethane product. High ratios of the isocyanate to polyol oligomer used for crosslinking may provide for a more rigid polyurethane product. In certain embodiments, polyols used to make rigid polyurethane products have molecular weights in the hundreds. In other embodiments, polyols used to make elastic and/or flexible polyurethanes have molecular weights up to ten thousand.

The following references contain information on the formulation, manufacture and uses of polyurethane foams and elastomers, and each of these references is incorporated herein by reference: U.S. Pat. No. 9,512,259; Vahid Sendijarevic, et al.; Polymeric Foams And Foam Technology, 2.sup.nd edition, Hanser Gardner Publications; 2004 (ISBN 978-1569903360) David Eaves; Handbook of Polymer Foams, Smithers Rapra Press; 2004 (ISBN 978-1859573884) Shau-Tarng Lee et al.; Polymeric Foams: Science and Technology, CRC Press 2006 (ISBN 978-0849330759) Kaneyoshi Ashida; Polyurethane and Related Foams: Chemistry and Technology, CRC Press; 2006 (ISBN 978-1587161599) Handbook of Thermoplastic Elastomers, William Andrew Publishers, 2007 (ISBN 978-0815515494) The Polyurethanes Book, J. Wiley & Sons, 2003 (ISBN 978-0470850411).

In certain embodiments, the processes include the use of polyols as disclosed in U.S. patent application Ser. No. 15/369,821, herein incorporated by reference. In certain embodiments, the polyol oligomer has a hydroxyl value of 20 to 350 mg KOH/g. In certain preferred embodiments, the polyol oligomer has a hydroxyl value of 20 to 200 mg KOH/g for providing high strength and water-resistant properties. In some embodiments, average molecular weight (Mn) of the polymer polyol to be used in the present invention is within a range of between about 500 g/mol and about 20,000 g/mol. The molecular weight distribution (Mw/Mn) is preferably within a range of 1 to 5.

In certain embodiments, the processes provide for production of flexible polyurethane comprising a polyether polyol and a polyester polyol derived from the copolymerization of one or more epoxides and carbon dioxide. In certain preferred embodiments for producing flexible polyurethane, the polyether polyol and the polyester polyol may be bonded by a diisocyanate and/or polyisocyanate. In certain embodiments, the flexible polyurethane contains from about 1 part to about 100 parts by weight of polyester polyol based on 100 parts of polyether polyol. In certain embodiments, the polyester polyol is present in such a quantity that the polyester polyol comprises about 5 parts, about 10 parts, about 20 parts, about 30 parts, about 40 parts, about 60 parts, about 80 parts, or about 100 parts, based on 100 parts of polyether polyol. In certain embodiments, the polyester polyol comprises poly(propylene carbonate). In certain embodiments, the polyester polyol present comprises poly(ethylene carbonate). In certain embodiments, the polyester polyol present comprises poly(ethylene-co-propylene carbonate).

In certain preferred embodiments, the processes of the present invention provide for rigid polyurethane products.

The embodiments described herein are not intended to be limited to the aspects shown, but are to be accorded the widest scope consistent with the principles and features disclosed herein.

What is claimed is:

1. A process for producing an isocyanate product comprising the steps:
   a. carbonylation of an epoxide reagent with a carbon monoxide reagent to produce a beta-lactone intermediate;

b. combining the beta-lactone intermediate with a nucleophile to produce an amide ring-opened intermediate or to produce an hydroxamic acid ring-opened intermediate; and c. contacting an amide ring-opened intermediate with a caustic base reagent in the presence of a halogen reagent to produce the isocyanate product or rearranging the hydroxamic acid ring-opened intermediate to produce the isocyanate product.

2. The process from claim 1 further comprising contacting the isocyanate product with an alcohol to produce a carbamate isocyanate derivative.

3. The process from claim 1 further comprising contacting the isocyanate product with water to produce an amine isocyanate derivative.

4. The process from claim 1 further comprising contacting the isocyanate product with a primary amine to produce a urea isocyanate derivative.

5. A process for producing an isocyanate product comprising the steps:
   a. carbonylation of an epoxide reagent with a carbon monoxide reagent to produce a beta-lactone intermediate;
   b. contacting the beta-lactone intermediate with a catalyst to produce an organic acid intermediate;
   c. reacting the organic acid intermediate with an azide reagent to produce an acyl azide intermediate; and
d. thermally decomposing the acyl azide intermediate to produce the isocyanate product.

6. The process from claim 5 further comprising contacting the isocyanate product with an alcohol to produce a carbamate isocyanate derivative.

7. The process from claim 5 further comprising contacting the isocyanate product with water to produce an amine isocyanate derivative.

8. The process from claim 5 further comprising contacting the isocyanate product with a primary amine to produce a urea isocyanate derivative.

9. A process for producing a diisocyanate product comprising the steps:
   a. carbonylation of an epoxide reagent with a carbon monoxide reagent to produce a beta-lactone intermediate;
   b. carbonylation of the beta-lactone intermediate with a carbon monoxide reagent to produce a succinic anhydride intermediate;
   c. combining the succinic anhydride intermediate with a nucleophile to produce an amide intermediate; and
   d. rearranging the amide intermediate in the presence of a halogen reagent with a caustic base reagent to produce the diisocyanate product.

10. The process from claim 9 wherein the amide intermediate is a diamide.

11. The process from claim 9 further comprising contacting the diisocyanate product with an alcohol to produce a carbamate diisocyanate derivative.

12. The process from claim 9 further comprising contacting the diisocyanate product with water to produce an amine diisocyanate derivative.

13. The process from claim 9 further comprising contacting the diisocyanate product with a primary amine to produce a urea diisocyanate derivative.

14. A process for producing an aromatic isocyanate product comprising the steps:
   a. carbonylation of an epoxide reagent with a carbon monoxide reagent to produce a beta-lactone intermediate;
   b. carbonylation of the beta-lactone intermediate with a carbon monoxide reagent to produce a succinic anhydride intermediate;
   c. oxidizing the succinic anhydride intermediate to provide an unsaturated four carbon intermediate;
   d. contacting the unsaturated four carbon intermediate with furan to provide a cyclohexene ring intermediate;
   e. combining the cyclohexene ring intermediate with a nucleophile to produce an amide intermediate; and
   f. rearranging the amide intermediate in the presence of a halogen reagent with a caustic base reagent to produce the aromatic isocyanate product.

15. The process from claim 14 further comprising the steps:
   a. dehydrating the cyclohexene ring intermediate to form a disubstituted benzene ring intermediate;
   b. combining the disubstituted benzene ring intermediate with a nucleophile to produce an amide intermediate; and
   c. rearranging the amide intermediate in the presence of a halogen reagent with a caustic base reagent to produce the aromatic isocyanate product.

16. The process from claim 15 further comprising contacting the aromatic isocyanate product with an alcohol to produce a carbamate aromatic isocyanate derivative.

17. The process from claim 15 further comprising contacting the aromatic isocyanate product with water to produce an amine aromatic isocyanate derivative.

18. The process from claim 15 further comprising contacting the aromatic isocyanate product with a primary amine to produce a urea aromatic isocyanate derivative.

19. A process for producing an aromatic isocyanate product comprising the steps:
   a. carbonylation of an epoxide reagent with a carbon monoxide reagent to produce a beta-lactone intermediate; and
      i b. reacting said beta-lactone intermediate with a furan reagent to produce an aromatic dicarboxylic acid intermediate;
      i c. reacting said aromatic dicarboxylic acid intermediate with an acyl chloride to produce a chlorocarbonyl intermediate;
      i d. reacting said chlorocarbonyl intermediate with a hydroxylamine to produce an aromatic hydroxamic acid intermediate; and
   i e. rearranging said aromatic hydrocamic acid intermediate to produce the aromatic isocyanate product, or
   ii b. rearranging said beta-lactone intermediate to produce an acrylic acid intermediate;
   ii c. reacting said acrylic acid intermediate with an isoprene intermediate to produce a cyclohexene-carboxylic acid intermediate;
   ii d. dehydro-aromatization of said cyclohexene-carboxylic acid intermediate to produce an aromatic dicarboxylic acid intermediate;
   ii e. reacting said aromatic dicarboxylic acid intermediate with an acyl chloride to produce a chlorocarbonyl intermediate;
   ii f. reacting said chlorocarbonyl intermediate with a hydroxylamine to produce an aromatic hydroxamic acid intermediate; and
   ii g. rearranging said aromatic hydrocamic acid intermediate to produce the aromatic isocyanate product.

20. A process for producing a polyurethane product comprising
  copolymerizing the diisocyanate product of claim 9 with a polyol oligomer to produce the polyurethane product.

\* \* \* \* \*